(12) United States Patent
Rubin

(10) Patent No.: US 12,175,659 B2
(45) Date of Patent: Dec. 24, 2024

(54) SYSTEM AND METHOD FOR PROVIDING STROKE LESION SEGMENTATION USING CONDITIONAL GENERATIVE ADVERSARIAL NETWORKS

(71) Applicant: KONINKLIJKE PHILIPS N.V., Eindhoven (NL)

(72) Inventor: Jonathan Rubin, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 432 days.

(21) Appl. No.: 17/312,428

(22) PCT Filed: Dec. 4, 2019

(86) PCT No.: PCT/EP2019/083577
§ 371 (c)(1),
(2) Date: Jun. 10, 2021

(87) PCT Pub. No.: WO2020/120238
PCT Pub. Date: Jun. 18, 2020

(65) Prior Publication Data
US 2022/0058798 A1 Feb. 24, 2022

Related U.S. Application Data

(60) Provisional application No. 62/778,459, filed on Dec. 12, 2018.

(51) Int. Cl.
*G06T 7/174* (2017.01)
*G06N 3/045* (2023.01)
(Continued)

(52) U.S. Cl.
CPC .......... *G06T 7/0012* (2013.01); *G06N 3/045* (2023.01); *G06T 7/174* (2017.01); *G06T 11/008* (2013.01);
(Continued)

(58) Field of Classification Search
CPC ..... G06T 7/0012; G06T 7/174; G06T 11/008; G06T 2207/10081; G06T 2207/10088;
(Continued)

(56) References Cited

U.S. PATENT DOCUMENTS

| 11,100,633 | B2 * | 8/2021 | Ngo Dinh | A61B 1/31 |
| 2012/0008838 | A1 * | 1/2012 | Guyon | G16H 50/20 |
| | | | | 382/128 |

(Continued)

OTHER PUBLICATIONS

Abulnaga et al: "Ischemic Stroke Lesion Segmentation in CT Perfusion Scans USIG Pyramid Pooling and Focal Loss"; arXiv:1811.01085v1, Nov. 2, 2018, 11 Page Article.
(Continued)

*Primary Examiner* — Shefali D Goradia
*Assistant Examiner* — D J Dhooge
(74) *Attorney, Agent, or Firm* — Sherry Austin

(57) ABSTRACT

A system and method for performing image processing. The method includes receiving an image of a first modality and a real image of a second modality, the image of the first modality and the image of the second modality capturing respective images of a same subject, applying a first trained model to the image of the first modality to generate an artificial image mimicking the image of the second modality, applying a second trained model to the artificial image mimicking the image of the second modality and data of the image of the first modality, and outputting at least one conclusion regarding the generated artificial image.

5 Claims, 4 Drawing Sheets

(51) Int. Cl.
 G06T 7/00 (2017.01)
 G06T 11/00 (2006.01)
 G16H 30/40 (2018.01)
(52) U.S. Cl.
 CPC ... *G16H 30/40* (2018.01); *G06T 2207/10081* (2013.01); *G06T 2207/10088* (2013.01); *G06T 2207/20084* (2013.01); *G06T 2207/30016* (2013.01); *G06T 2207/30096* (2013.01); *G06T 2207/30104* (2013.01); *G06T 2211/408* (2013.01)
(58) Field of Classification Search
 CPC . G06T 2207/20084; G06T 2207/30016; G06T 2207/30096; G06T 2207/30104; G06T 2211/408; G16H 30/40; G06N 3/045
 See application file for complete search history.

(56) References Cited

U.S. PATENT DOCUMENTS

| | | | |
|---|---|---|---|
| 2016/0148372 A1* | 5/2016 | Itu | G06F 18/217 |
| | | | 382/128 |
| 2017/0046839 A1* | 2/2017 | Paik | G06V 10/84 |
| 2018/0225823 A1* | 8/2018 | Zhou | G06T 7/11 |

OTHER PUBLICATIONS

Ben-Cohen et al:"Cross-Modality Synthesis From CT to PET Using FCN and GAN Networks for Improved Automated Lesion Detection"; arXiv:1802.07846v2, Jul. 23, 2018, 9 Page Article.
Biesbroek et al: "Diagnostic Accuracy of CT Perfusion Imaging for Detecting Acute Ischemic Stroke:A Systematic Review and Meta-Analysis"; Cerebrovasc Dis 2013, 35:493-501.
Cereda et al: "A Benchmarking Tool to Evaluate Computer Tomography Perfusion Infarct Core Predictions Against a DWI Standard"; Journal of Cerebral Blood Flow & Metabolism, 2016, vol. 36 (10), pp. 1780-1789.
Chartsias et al: "Adversarial Image Synthesis for Unpaired Multi-Modal Cardiac Data"; Sashimi 2017, LNCS 10557, pp. 3-13, 2017.
Dai et al: "SCAN:Structure Correcting Adversarial Network for Organ Segmentation in Chest-X-Rays"; arXiv:1703.08770v2, Apr. 10, 2017 10 page article.
Jin et al: "CT-Realistic Lung Nodule Simulation From 3D Conditional Generative Adversarial Networks for Robust Lung Segmentation"; arXiv:1806.04051V1, Jun. 11, 2018.
Gillebert et al: "Automated Delineation of Stroke Lesions Using Brain CT Images"; NeuroImage: Clinical 4 (2014) pp. 540-548.
Goodfellow et al: "Generative Adversarial Nets"; Part of Advnaces in Neural Information Processing Systems 27 (NIPS 2014), Edited by Z. Ghahramani, M. Welling, C. Cortes, N. Lawrence and K.Q. Weinberger, Abstract.
He et al: "Deep Residual Learning for Image Recognition"; arXiv:1512.03385v, Dec. 10, 2015, p. 1-12.
Isola et al: "Image-to-Image Translation With Conditional Adversarial Networks"; arXiv:1611.07004v3, Nov. 26, 2018, pp. 1-13.
PCT/EP2019/083577 ISR & Written Opinion, Jan. 24, 2020, 14 Page Document.
Lau et al: "ScarGAN: Chained Generative Adversarial Networks to Simulate Pathological Tissue on Cardiovascular MR Scans"; arXiv:1808.04500V!, Aug. 14, 2018.
Mahapatra et al: "Deformable Medial Image Registratio Using Generative Adversarial Networks"; 2018 IEEE 15th International Symposium on Biomedical Imaging (ISBI 2018), Apr. 4-7, 2018, pp. 1449-1453.
Maier et al: "Isles 2015-A Public Evaluation Benchmark for Ischemic Stroke Lesion Segmentation From Multipectral MRI"; Medical Image Analysis 35 (2017) pp. 250-269.
Mirza: "Conditional Generative Adversarial Nets"; arXiv:1411.1784v1, Nov. 6, 2014, 7 Page Article.
Nie et al: "Medical Image Synthesis With Context-Aware Generative Adversarial Networks"; arXiv:1612.05362v1, Dec. 16, 2016, 12 Page Article.
Oksuz et al: "Cardiac MR Motion Artefact Correction From K-Space Using Deep Learning-Based Reconstruction"; Lecture Notes in Computer Scence, 2018, pp. 21-29.
Russakovsky et al: "ImageNET Large Scale Visual Recognition Challenge"; Int J. Comput Vis (2015) 115:211-252.
Ulyanov et al: "Instance Normalization: the Missing Ingredient for Fast Stylization"; arXiv:1607.08022v3, Nov. 6, 217, 6 Page Article.
Winzeck et al: "Isles 2016 and 2017—Benchmarking Ischemic Stroke Lesion Outcome Prediction Based on Multispectral MRI"; Frontiers in Neurology, vol. 9, Article 679, pp. 1-20, Sep. 13, 2018.
Wolterink et al: "Blood Vessel Geometry Synthesis Using Generative Adversarial Networks"; arXiv:1804.04381v1, Apr. 12, 2018, 10 Page Article.
Wolterink et al: "Deep MR to CT Synthesis Using Unpaired Data"; arXiv:1708.01155v1, Aug. 3, 2017, 10 Page Article.
Yu et al: "Multi-Scale Context Aggregation by Dilated Convolutions"; Published as a Conference Paper at ICLR 2016, arXiv:1511.07122v3, Apr. 30, 2016, 13 Page Article.
Zhu et al: "Unpaired Image-to-Image Translation Using Cycle-Consistent Adversarial Networks";arXiv:1703.10593v7, Aug. 24, 2020, 18 Page Article.

* cited by examiner

SYSTEM AND METHOD FOR PROVIDING STROKE LESION SEGMENTATION USING CONDITIONAL GENERATIVE ADVERSARIAL NETWORKS

CROSS-REFERENCE TO PRIOR APPLICATIONS

This application is the U.S. National Phase application under 35 U.S.C. § 371 of International Application No. PCT/EP2019/083577, filed on Dec. 4, 2019, which claims the benefit of U.S. Provisional Patent Application No. 62/778,459, filed on Dec. 12, 2018. These applications are hereby incorporated by reference herein.

The present disclosure relates generally to a system and method for performing image processing, and more specifically, for providing stroke lesion segmentation using Conditional Generative Adversarial Networks (CGAN).

Ischemic stroke is caused by partial or total restriction of blood supply to part of the brain, often caused by blood clots. During an acute stroke, prolonged ischemia results in irreversible tissue death. Decisions about ischemic stroke therapy are highly time-sensitive and rely on distinguishing between the infarcted core tissue and hypo perfused lesions performed through segmentation around the penumbra, or the area surrounding the ischemic event. Traditionally, segmentation is performed manually by a radiologist and is time consuming. As such, automated methods that can locate and segment ischemic stroke lesions can aid clinician decisions about acute stroke treatment. Computed Tomography Perfusion (CTP), where contrast agents are injected during a CT exam to obtain perfusion maps, has been used to triage stroke patients and has advantages in cost, speed and availability over diffusion-weighted magnetic resonance imaging (DWI), which may readily capture ischemic core regions as hyperintensities on a Magnetic Resonance (MR) image. CTP provides detailed information about blood flow within the brain and can determine areas that are inadequately perfused with blood. However, CTP has a lower signal to noise ratio and has difficulty identifying the ischemic core compared to DWI, where infarcted core brain tissue readily shows up as hyperintense regions.

In view of the above discussion, there is a need for performing image processing that would overcome the deficiencies noted above between DWI and CTP systems.

It would therefore be advantageous to provide a solution that would overcome the challenges noted above.

The subject matter disclosed herein is particularly pointed out and distinctly claimed in the claims at the conclusion of the specification. The foregoing and other objects, features, and advantages of the disclosed embodiments will be apparent from the following detailed description taken in conjunction with the accompanying drawings.

Figure 1:
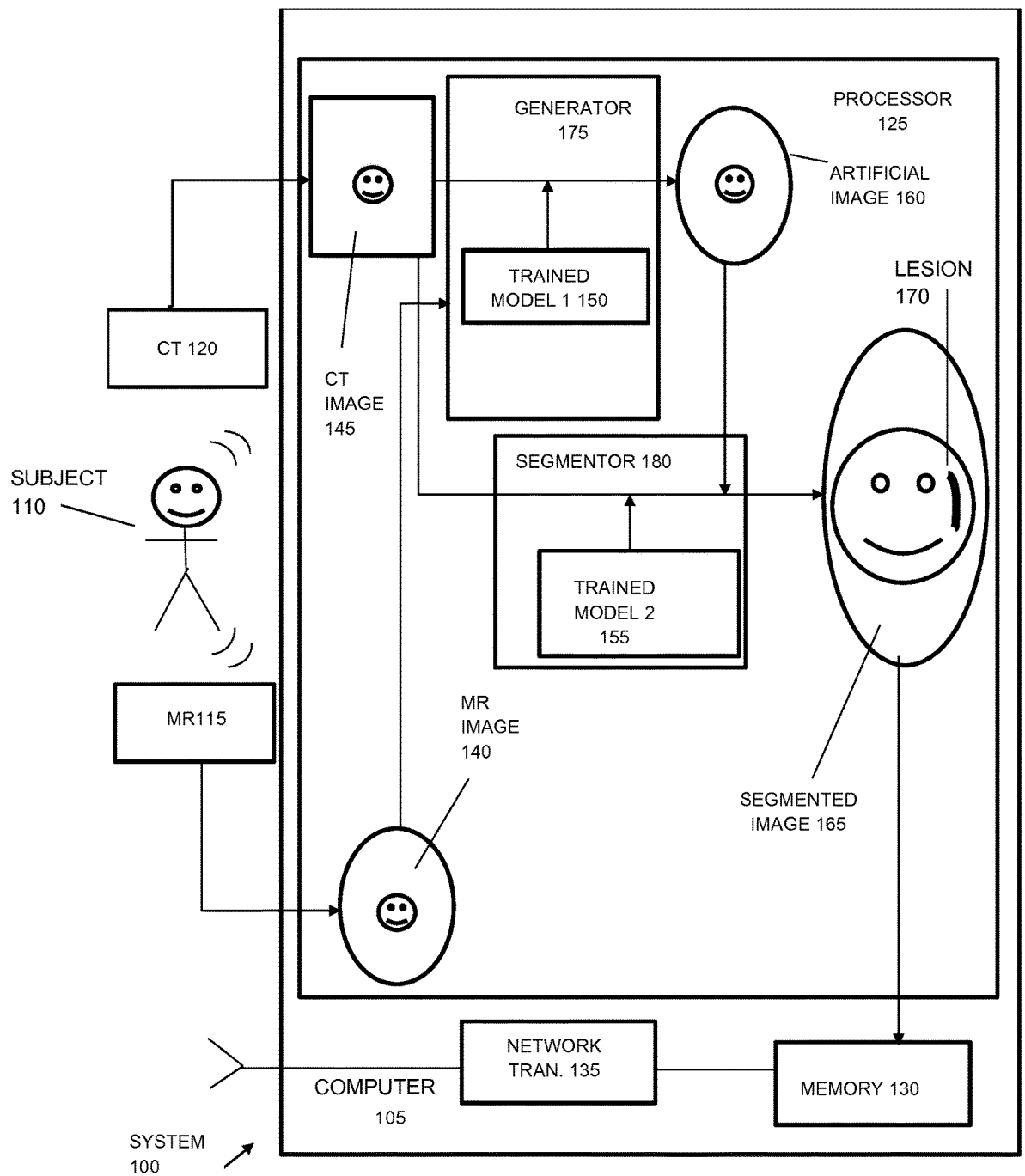
FIG. 1 is a block diagram of a system for providing stroke lesion segmentation, according to an embodiment herein.

Various embodiments are described more fully hereinafter with reference to the accompany drawings. It is important to note that the embodiments disclosed herein are only examples of the many advantageous uses of the innovative teachings herein. Alternate embodiments will be apparent to those skilled in the pertinent art upon reading this disclosure and may be constructed and practiced without departing from the scope or spirit of the disclosure. In general, statements made in the specification of the present application do not necessarily limit any of the various embodiments. Moreover, some statements may apply to some inventive features but not to others. In general, unless otherwise indicated, singular elements may be in plural and vice versa with no loss of generality. In the drawings, like numerals refer to like parts through several views.

The various disclosed embodiments include a method and system for performing image processing. The method includes receiving an image of a first modality and a real image of a second modality, the image of the first modality and the image of the second modality capturing respective images of a same subject, applying a first trained model to the image of the first modality to generate an artificial image mimicking the image of the second modality, applying a second trained model to the artificial image mimicking the image of the second modality and data of the image of the first modality, and outputting at least one conclusion regarding the generated artificial image. That is, various embodiments train generative adversarial networks using deep learning to learn a conditional mapping that maps Computer Tomography Perfusion (CTP) infarcted core regions to more clearly delineated hyperintense areas in generated Magnetic Resonance (MR) scans. Various embodiments utilize a dataset of paired Computer Tomography (CT) and MR scans, whereby each acute stroke patient undergoes a back-to-back CTP and Magnetic Resonance Imaging (MRI) Diffusion Weighted Imaging (DWI) imaging-within three hours of each other. Each CT scan may be co-registered with its corresponding DWI. Perfusion maps may be derived from each CT scan including cerebral blood flow (CBF), cerebral blood volume (CBV), mean transit time (MTT) and time to peak of the residue function (Tmax).

Various embodiments also employ an image-to-image translation framework and modify it to accept multi-modal CT perfusion maps as input. After training conditional generative adversarial networks (CGANs) to reconstruct MR from CT perfusion maps, Fully Convolutional Neural Networks (FCN) are trained to perform semantic segmentation of infarcted core tissue and compare whether performance can be improved by including the generated MR as an extra channel of information to the network.

FIG. 1 is a block diagram of a system 100 for providing stroke lesion segmentation, according to an embodiment. The system includes a computer 105, such as a Personal Computer (PC), a first imaging modality 120, which may be, for example, a Computed Tomography (CT) device. For training purposes, a second imaging modality 115, which may be, for example, a Magnetic Resonance Imaging (MRI) device, may also be provided. A first image 145 (e.g. CT scan) and a second image 140 (e.g., MR scan) may be generated by the first imaging modality 120 and the second imaging modality 115, respectively, and sent to the computer 105 for further processing.

The computer 105 further includes a processor 125, a memory 130, and a network transmitter 135. The processor 125 may be programmed to include a generator 175 and a segmentor 180. Within a generator 175, a first trained model 150 is included and may be applied to the first image 145, resulting in an artificial image 160. Within the segmentor 180, a second trained model 155 may be included and may be applied to various incoming images, with the processed result outputted as a segmented image 165, where a lesion 170 on the subject 110 may be identified. The memory 130 stores the segmented image 165, while the network transmitter 135 may send the stored segmented image 165 into the internet, or the cloud, for further processing or viewing.

In operation, the system 100 takes the first image 145 via the first modality 120, which may come from the CT scan, and the second image 140 via a second modality 115, which may come from an MR scan. The images 145 and 140 of the first modality 120 and the second modality 115, respectively, capture respective images of a subject 110, which may be a patient.

Next, the first image 145 from the first modality 120 is sent to the processor 125 of the computer 105, where the generator 175 applies the first trained model 150 to the first image 145 of the first modality 120 to generate the artificial image 160, which mimics the second image 140 taken by the second modality 115. The second image 140 taken by the second modality 115 may also be separately sent to the processor 125 of the computer 105.

Thereafter, the artificial image 160, together with the original first image 145 and the original second image 140, may be sent to the segmentor 180, where the second trained model 155 is applied to at least one of the artificial image 160 or data gathered from the first image 145 received from the respective generator 175 and first modality 120. Based on the processing performed here, the details of which will be elaborated below, the segmented image 165 is output, where the lesion 170 on the subject 110 may be identified.

The segmented image 165 may then be output and stored in the memory 130, and may also be transmitted via the network transmitter 135 for further processing or viewing by physicians.

Figure 2:
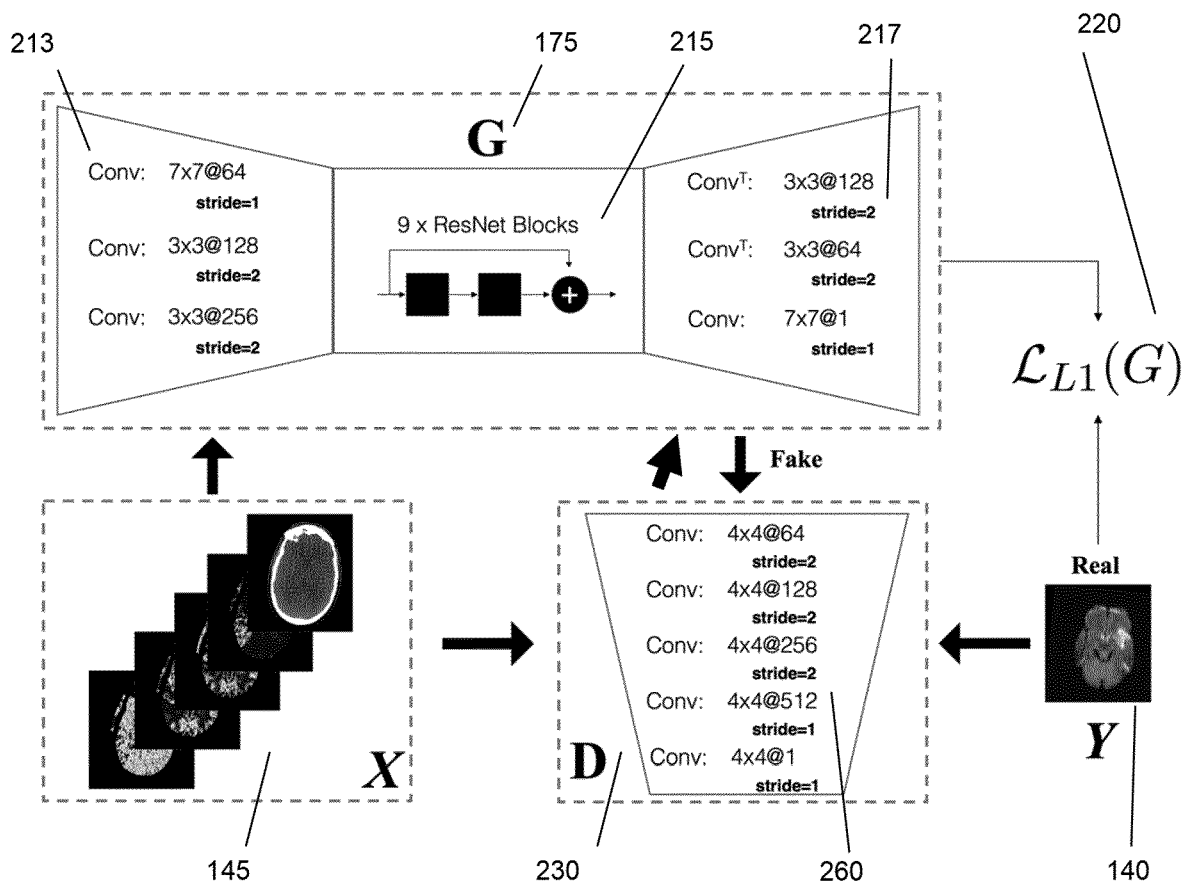
FIG. 2 is a detailed block diagram of a trained model of the image processing system for providing stroke lesion segmentation, according to an embodiment herein.

FIG. 2 illustrates a detailed block diagram of the first trained model 150 of the image processing system 100 for providing stroke lesion segmentation. Before the use of the first trained model 150, it is trained based on existing images, which may be from CT and/or MR devices. A captured CT image is transformed to artificial "MR" images that mimic actual or real MR images. The artificial MR image is compared to "real" MR images, and the first trained model 150 learns the differences between the artificial and real MR images. A feedback loop is generated where the first trained model 150 adapts to improve on the artificial image based on the comparison until there are no discernible differences between the artificial and the real MR images.

Deep learning techniques are involved in the training of the models, so that from a CT image, artificial images 160 that mimic real MR images may be replicated through an adversarial network.

In general, Generative Adversarial Networks (GAN) work by training both a generator network G(z) such as the generator 175 and a discriminator network D such as the discriminator 230. The generator network, G(z), attempts to generate outputs that resemble, or mimic images, y that are captured from another modality, such as the second modality 115 (e.g., Magnetic Resonance Imaging (MRI)), from a distribution of training data. A generator network is represented by the equation, G: z→y, where z is a random noise vector that is added by including a "Dropout" operation in the generator network G(z). This has the effect of setting some weights to 0 randomly during training.

The discriminator network D (discriminator 230), on the other hand, may receive either a real image, D(y), or a generated (i.e., "fake") D(G(z) image output from the generator 175 as input, and attempts to distinguish whether the input is real (images resulting from the true underlying data distribution (e.g., the second modality 115 MR)) or fake (images created by the generator 175). A loss is determined from analysis performed by the discriminator 230.

As an example, for the task of generating artificial MR images 160 that are conditioned on CT Perfusion (CTP) inputs from the first modality 120, various embodiments may adopt a Conditional Generative Adversarial Networks (CGAN) formulation. CGANs alter the generator 175 such that the image created by the generator 175 is conditioned on an original input image 145, which is represented by the equation:

$$G: x, z \rightarrow y,$$

where x is the input image and z is once again a random noise vector. The discriminator function D (which will be described in more detail below), is also updated to accept the conditional image, the real image, y, or fake input, G(x,z), created by the generator as input. The discriminator function D gives the output of the discriminator 230. A value close to 1 indicates the discriminator 230 'believes' the input is real. In contrast, a value close to 0 indicates the discriminator 'believes' the input is fake. The first component is the average value obtained when the discriminator is given real data. The second component is the average value obtained when the discriminator is given fake data.

The full objective function for the conditional generator, or the CGAN loss, is given in Equation (1) Below:

$$L_{CGAN}(G,D) = E_{x,y \sim p_{data}(x,y)}[\log(D(x,y))] + E_{x \sim p_{data}(x), z \sim p_z(z)}[\log(1 - D(x, G(x,z)))] \quad \text{Equation (1)}$$

Here, z is introduced into the generator network (G(z)) in the form of a dropout at both training and test time. That is, the dropout is an operation that can be applied when training deep neural networks. As the network trains, a neuron can be randomly set to 0 (dropped out). This ensures the network duplicates channels of information as it learns, so it does not rely on a single neuron activation to make its decisions.

The final objective function for training the CT-to-MR translation model combines both the global LCGAN(G,D) loss together with an additional L1 loss term, as illustrated by Equation (2) below, that captures the local per-pixel reconstruction error. The combined objective function is given in Eq (3), where λ is selected as a hyperparameter.

$$L_{L1}(G) = E_{x,y \sim p_{data}(x,y), z \sim p_z(z)}[\|y - G(x,z)\|_1] \quad \text{Equation (2)}$$

and $$G^* = \arg\min\max = L_{CGAN}(G,D) + \lambda L_{L1}(G) \quad \text{Equation (3)}$$

is the Generator Architecture.

In an embodiment, as illustrated by FIG. 2, a high level overview of the generator architecture for the generator 175, (G) is shown. The generator 175 is configured to generate samples from a same distribution. Here, 5-channel 256×256 CT perfusion image slices 145 (X) captured from a Computed Tomography (CT) scan performed by the first modality 120, are stacked together with the Cerebral Blood Flow (CBF), Cerebral Blood Volume (CBV), Maximum Transit Time (MTT), and Time to maximum point (Tmax) perfusion maps. These are flow and volume measurements of contrast agents within the brain vessels during a CT perfusion scan. First, three initial convolution operations 213 are applied to the received perfusion slices 145. That is, the standard operation of a convolutional neural network is a convolution. It is effectively the task of learning a filter (set of numbers/weights), which activate (become larger) when relevant information is present within an input. Therefore, convolution operations are effectively matrix multiplications stacked together in layers. As such, various choices can be made about number of filters to use and their sizes.

For example, the size and number of convolutional kernels are shown in FIG. 2 and take on a notation of: nxn@f, where n is the kernel size and f the number of kernels. Downsampling, which reduces the size of an input image, (e.g. an image with a width and height that is 256×256 pixels can be downsampled to 128×128 pixels), is achieved via strided convolution 213. This is followed by processing by 9 ResNet blocks 215, where a ResNet block is a residual block that consists of the following set of convolution operations: Conv-InstanceNorm-ReLU-Dropout-Conv-InstanceNorm. Before each convolution operation (Cony) in the block, reflection padding with size 1 is added to each border of the input to deal with the edges of images as convolutional filters are applied, instead of just multiplying filters by zero. Also, the number of feature maps stays constant at 256, throughout the 9 ResNet blocks 215, as does their spatial resolution. Upsampling is achieved in the generator 175 via fractionally strided convolutions (ConvT) 217, as shown in FIG. 2. Here, upsampling is the opposite of down-sampling, where the image is growing instead of shrinking. Convolution operations can also be used to grow an image. Finally, a 1×256×256 single channel derived or artificial image 160 of the MR slice image is output from the generator 175 after the ConvT 217 is performed.

Discriminator Architecture

Various embodiments utilize a generator 230 to determine whether the input comes from a real image 140 or an artificial image 160. Here, a convolutional PatchGAN discriminator 230 models high frequency image structure in local patches and penalizes incorrectness at the N×N patch-level. This is, combined with an L1 loss term, LL1, that enforces low frequency correctness as determined from Equation 1 (i.e. the loss component that captures how well the discriminator can tell the difference between real and fake images). A high-level overview of the discriminator 230, D, is depicted in FIG. 2. This conditional discriminator 230 accepts either "real" MR slice images 140 (Y), D(x, y) that generate a three-dimensional image, or generated artificial MR slice images 160 from the generator 175 (G), D(x, G(x, z)), together with the original CT data and CT perfusion maps of the CT image 145 (X), x∈R5×256×256. CTP data and 'real' or 'fake' MR slices are stacked together in the channel dimension resulting in 6×256×256 inputs being processed by the PatchGAN discriminator 230. All convolutions use a kernel size of 4×4, with downsampling once again being handled via strided convolution 260. Excluding the first and last convolution shown in FIG. 2, each convolution is followed by an instance normalization operation and LeakyReLU activation (not shown) with a negative slope coefficient of 0.2. A 30×30 map of discriminator activations is output by the discriminator network 230, where each activation captures a 70×70 receptive field of overlapping patches from input channels. The final discriminator output is given by an average of this activation map.

CGAN Implementation Details

Next, the CT-to-MR CGAN may be trained by alternating one gradient descent step of the discriminator 230, followed by one gradient descent step for the generator 175, to train deep neural networks. Derivative of loss is calculated, and this information is backpropagated to every neuron in the network. A batch size of 1 may be used for training all networks. A dropout rate of 0.5 (between 0 and 1) may be applied within each ResNet block 215 in the generator 175. Here, the higher that the dropout rate is set, the more that the data will be taken out. Within the final loss function, G*, a value of λ=100 may be used to weight the combination of both L1 loss and that supplied from LCGAN. To perform gradient descent (i.e., to train the network), Adam optimization may be used, for example, for training both the generator 175 and discriminator 230 with learning rates set to 2e-4 and momentum parameters β1=0.5, β2=0.999.

That is, to train neural networks well, a lot of data is needed. During data augmentation, many different versions of an image are produced on the fly (e.g., by rotating the image, translating it around, etc.). This helps the network to generalize image inputs that may not look exactly like the original input images. Here, Adam optimization alters how network weights are updated during training. Also, Affine data transformations consisting of translation, rotation and scaling may be used for augmentation. Each network may be trained for a total of 200 epochs using PyTorch on a single Nvidia P100 GPU, for example.

In other words, a feedback loop exists between the generator 175 and discriminator 230, where the discerned differences between real MR image 140 and the artificial images from the discriminator along with the identification of real/artificial image determination and loss values are fed back to the generator 175, where adaptions can be made by the generator 175 to improve the artificial image 160 by increasing or decreasing weight on the differentiated areas of the artificial image 160. The artificial image 160 is then sent back to discriminator for additional differentiation and hyperintensity mapping between the real images 140 and the weighed images 160, until the discriminator 230 can no longer identify differences between the real MR image 140 and the artificial image 160.

That is, the process repeats between discriminator 230 and generator 175 to improve image until loss output L1, or the distance between real pixels and the generated pixels (between values of 0 and 1) of the respective images from the discriminator are minimized so that the discriminator 230 may no longer perceive a difference in comparing between the real MR image 140 and the artificial image 160 (replicated MR image). Upon completion of training, the first trained model 150 may now be applied to create artificial images 160 from subsequent CT images 145 that mimic real MR images 140, without having to take additional real MR image 140 of the subject 110.

Ischemic Core Segmentation FCN Model

The final ischemic core segmentation network, or segmentor 180 employs a Fully Convolutional neural Network (FCN) to serve as the second trained model 155 and utilizes pyramid pooling for capturing global and local context. The FCN component of the architecture relies on residual connections to aid information flow during training and dilated convolution to cover larger receptive field sizes from the network inputs. Here, segmentation masks created by radiologists are given as ground truth. The task is to feed these examples to a neural network and reward the neural network when it produces the same segmentations, and penalize the neural network when the produced segmentations are different. Focal loss, which is a slight alteration in the loss function that allows the network to focus on harder cases to evaluate and avoid over optimizing easy cases, is used as the loss function to attempt to learn the varying shapes of the lesion masks and effectively deal with the class imbalance between ischemic core and non-infarct areas, where there are very few stroke pixels and a lot of normal pixels. Here, focal loss is especially useful when there is a lot of class imbalance, (i.e. very few stroke pixels and a lot of normal pixels). Also, by supplying ground truth images that demonstrate different stroke lesion patterns, the more variety of patterns the network sees, the better the segmentor 180 will be able to reproduce the range of appropriate patterns.

The second trained model, the segmentor 180, or segmentation network, is trained using transfer learning, beginning with weights that have been trained on natural images from ImageNet, for example, and come from software that is available as open source software. Here, the transfer learning approach involves beginning with a network that has already been trained on some other task, (e.g. a set of natural images) and then training it on another task, (e.g. a set of CT images). The alternative is to train the network without any prior knowledge. However, the transfer learning approach is quicker to train. During training, data augmentations are created using standard affine transformations including rotation [−10°, 10°], translation [−10%, 10%] and scaling [0.9, 1.1].

Two FCNs may be trained to perform the final ischemic core segmentation using the artificial images 160 generated after applying the first trained model. The network architecture and training details generally remain the same in some embodiments. The only difference between the networks is the inputs that are fed to them, with one network that doesn't include the generated 'fake' MR data, and the other one that does include the generated MR data. Inputs to the first FCN network may consist of 5-channel 2D slices containing the original CT image 145, together with its corresponding CBF, CBV, TTP and MTT perfusion maps. Inputs to the second FCN network may be augmented with an extra channel of information that contains the derived MR slice (i.e., the artificial image 160)—generated by the CT-to-MR GAN or the generator 175, conditioned on the 5-channel CTP input.

Upon being trained, the FCN may now be applied to perform segmentation between the artificial image 160 and data from the first CT image 145, using a binary process to discern differences between the two images. The differences identify the ischemic areas of the artificial image 160, in ways similar to those identified by a real image 140 captured with an MR imager.

Certain embodiments presented show that FCNs trained with combined CTP and generated MR inputs in the image-to-image translational manner may be able to outperform networks trained without extra derived MR information on a range of metrics. That is, while maintaining the cost, speed, and availability of CTP over DWI while providing detailed information about blood flow within the brain, and having the ability to determine areas that are inadequately perfused with blood, signal to noise ratio similar to that of DWI with respect to infarcted core brain tissue may be maintained, so that detailed images of the ischemic core areas may readily be viewable using only CTP images.

Figure 3:
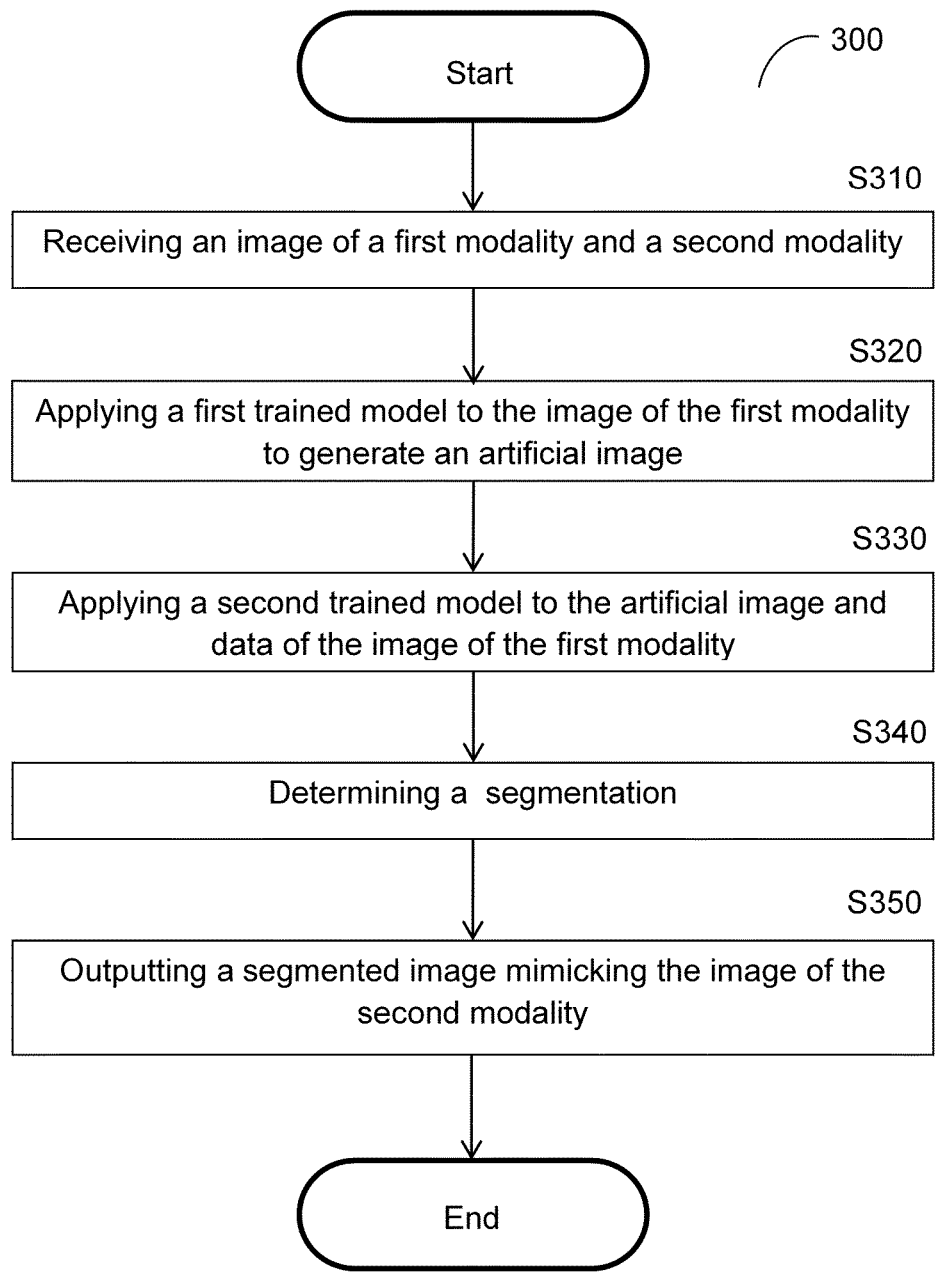
FIG. 3 is a flowchart for a method of providing stroke lesion segmentation, according to an embodiment herein.

FIG. 3 is a flowchart for a method of providing stroke lesion segmentation performed by the system 100, according to an embodiment. At S310, the system 100 receives an image of a first modality, which may come from a CT scan, and an image of a second modality, which may come from an MR scan. The image of the first modality and the image of the second modality capture respective images of a subject 110, such a patient having the lesion 170.

Next, at S320, a first trained model is applied to the image of the first modality to generate an artificial image mimicking the image of the second modality. This first trained model may be a network such as the GAN, or more specifically, a CGAN.

Afterwards, at S330 a second trained model is applied to both the artificial image mimicking the image of the second modality, to which the first trained model was previously applied, and data from the image of the first modality. This second trained model may be an FCN.

At S340, determining a segmentation of the image is performed. Finally, at S350, the segmented image is outputted from the system 100.

By performing the method as shown, certain embodiments are able to outperform networks trained without extra derived MR information on a range of metrics. That is, while maintaining the cost, speed, and availability of CTP over DWI, providing detailed information about blood flow within the brain, and having the ability to determine areas that are inadequately perfused with blood, signal to noise ratio similar to that of DWI with respect to infarcted core brain tissue may be maintained.

Certain embodiments described above provide a system and method for an improved segmentation of CT medical images of infarcted core areas that are modified through trained neural network models to mimic MR images that normally provide for superior 3D imaging and better highlight areas of interest as compared to CT images without application of trained neural network models. Certain embodiments allow for data to be used to easily identify hyperintense stroke and ischemic tissue similar to that achieved through MRI, without the cost and inconveniences associated with real MRI imaging.

Figure 4:
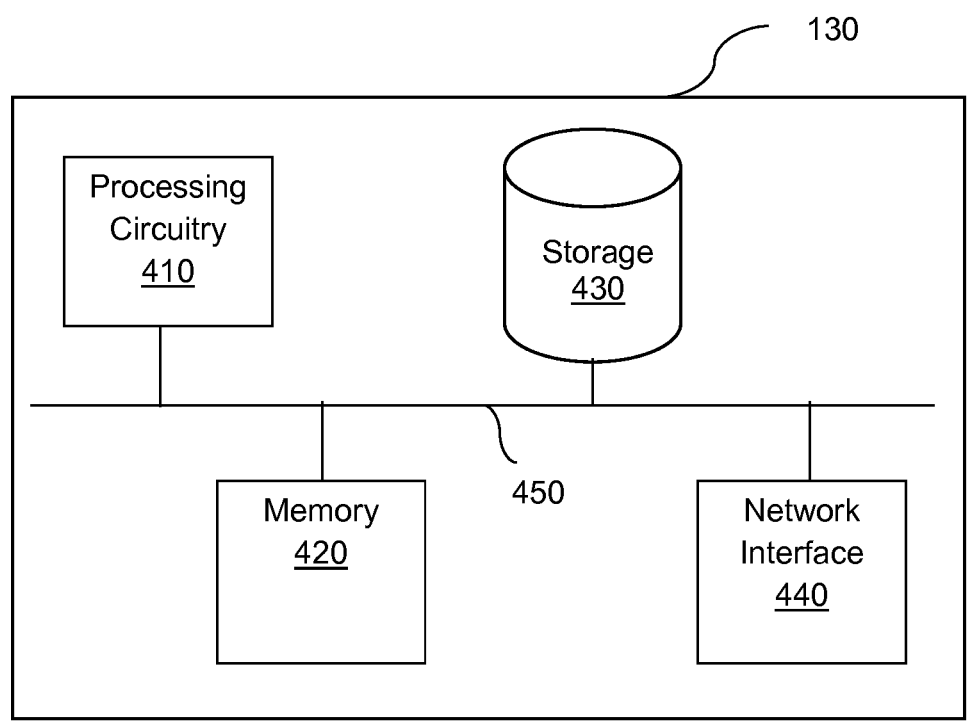
FIG. 4 is a schematic diagram of a system for providing stroke lesion segmentation, according to an embodiment herein.

FIG. 4 is an example schematic diagram of a system 130 for providing stroke lesion segmentation, according to an embodiment. The system 130 includes a processing circuitry 410 coupled to a memory 420, a storage 430, and a network interface 440. In an embodiment, the components of the system 130 may be communicatively connected via a bus 450.

The processing circuitry 410 may be realized as one or more hardware logic components and circuits. For example, and without limitation, illustrative types of hardware logic components that can be used include field programmable gate arrays (FPGAs), application-specific integrated circuits (ASICs), Application-specific standard products (ASSPs), system-on-a-chip systems (SOCs), general-purpose microprocessors, microcontrollers, digital signal processors (DSPs), and the like, or any other hardware logic components that can perform calculations or other manipulations of information.

The memory 420 may be volatile (e.g., RAM, etc.), non-volatile (e.g., ROM, flash memory, etc.), or a combination thereof. In one configuration, computer readable instructions to implement one or more embodiments disclosed herein may be stored in the storage 430.

In another embodiment, the memory 420 is configured to store software. Software shall be construed broadly to mean any type of instructions, whether referred to as software, firmware, middleware, microcode, hardware description language, or otherwise. Instructions may include code (e.g., in source code format, binary code format, executable code format, or any other suitable format of code). The instructions, when executed by the processing circuitry 410, cause the processing circuitry 410 to perform the various processes described herein.

The storage 430 may be magnetic storage, optical storage, and the like, and may be realized, for example, as flash memory or other memory technology, CD-ROM, Digital Versatile Disks (DVDs), or any other medium which can be used to store the desired information.

The network interface 440 allows the system 130 to communicate for the purpose of, for example, receiving data, sending data, and the like.

It should be understood that the embodiments described herein are not limited to the specific architecture illustrated in FIG. 4, and other architectures may be equally used without departing from the scope of the disclosed embodiments.

The various embodiments disclosed herein can be implemented as hardware, firmware, software, or any combination thereof. Moreover, the software is preferably implemented as an application program tangibly embodied on a program storage unit or computer readable medium consisting of parts, or of certain devices and/or a combination of devices. The application program may be uploaded to, and executed by, a machine comprising any suitable architecture. Preferably, the machine is implemented on a computer platform having hardware such as one or more central processing units ("CPUs"), a memory, and input/output interfaces. The computer platform may also include an operating system and microinstruction code. The various processes and functions described herein may be either part of the microinstruction code or part of the application program, or any combination thereof, which may be executed by a CPU, whether or not such a computer or processor is explicitly shown. In addition, various other peripheral units may be connected to the computer platform such as an additional data storage unit and a printing unit. Furthermore, a non-transitory computer readable medium is any computer readable medium except for a transitory propagating signal.

All examples and conditional language recited herein are intended for pedagogical purposes to aid the reader in understanding the principles of the disclosed embodiment and the concepts contributed by the inventor to furthering the art, and are to be construed as being without limitation to such specifically recited examples and conditions. Moreover, all statements herein reciting principles, aspects, and embodiments of the disclosed embodiments, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

It should be understood that any reference to an element herein using a designation such as "first," "second," and so forth does not generally limit the quantity or order of those elements. Rather, these designations are generally used herein as a convenient method of distinguishing between two or more elements or instances of an element. Thus, a reference to first and second elements does not mean that only two elements may be employed there or that the first element must precede the second element in some manner. Also, unless stated otherwise, a set of elements comprises one or more elements.

As used herein, the phrase "at least one of" followed by a listing of items means that any of the listed items can be utilized individually, or any combination of two or more of the listed items can be utilized. For example, if a system is described as including "at least one of A, B, and C," the system can include A alone; B alone; C alone; 2A; 2B; 2C; 3A; A and B in combination; B and C in combination; A and C in combination; A, B, and C in combination; 2A and C in combination; A, 3B, and 2C in combination; and the like.

What is claimed is:

1. A method for performing medical image processing, comprising: receiving a first image from a Computer Tomography (CT) scan of a patient; applying a trained conditional generator model to the first image to generate an artificial Magnetic Resonance Imaging (MRI) scan image of the patient, wherein the conditional generator model is trained by a conditional generative adversarial network (cGAN); applying a second trained model to the artificial MRI scan image and the first image to generate segmentations of each of the artificial MRI scan image and the first image; and outputting at least one conclusion regarding the artificial MRI scan image, wherein the at least one conclusion is generated by performing a comparison between the segmentations of the artificial MRI scan image and the segmentations of the first image, wherein the at least one conclusion is an identification of an ischemic lesion in the artificial MRI scan image.

2. The method of claim 1, wherein the second trained model is a Fully Convolutional Network (FCN).

3. A non-transitory computer readable medium having stored thereon instructions for causing a processing circuitry to execute a process of performing medical image processing, the process comprising: receiving a first image from a Computer Tomography (CT) scan of a patient; applying a trained conditional generator model to the first image to generate an artificial MRI scan image of the patient, wherein the conditional generator model is trained by a conditional generative adversarial network (cGAN); applying a second trained model to the artificial MRI scan image and the first image to generate segmentations of each of the artificial MRI scan image and the first image; and outputting at least one conclusion regarding the artificial MRI scan image, wherein the at least one conclusion is generated by performing a comparison between the segmentations of the artificial MRI scan image and the segmentations of the first image, wherein the at least one conclusion is an identification of an ischemic lesion in the artificial MRI scan image.

4. A system for performing image processing, comprising: a processing circuitry; and a memory containing instructions that, when executed by the processing circuitry, configure the system to: receive a first image from a Computer Tomography (CT) scan of a patient; apply a trained conditional generator model to the first image to generate an artificial MRI scan image of the patient, wherein the conditional generator model is trained by a conditional generative adversarial network (cGAN); apply a second trained model to the artificial MRI scan image and the first image to generate segmentations of each of the artificial MRI scan image and the first image; and output at least one conclusion regarding the artificial MRI scan image, wherein the at least one conclusion is generated by performing a comparison between the segmentations of the artificial MRI scan image and the segmentations of the first image, wherein the at least one conclusion is an identification of an ischemic lesion in the artificial MRI scan image.

5. The system of claim 4, wherein the second trained model is a Fully Convolutional Network (FCN).

* * * * *